(12) United States Patent
Hanano (10) Patent No.: US 10,857,248 B2
(45) Date of Patent: Dec. 8, 2020

(54) METHOD OF STERILIZING BEVERAGE DISPENSER AND BEVERAGE DISPENSER

(71) Applicant: SUNTORY HOLDINGS LIMITED, Osaka (JP)

(72) Inventor: Hirofumi Hanano, Tokyo (JP)

(73) Assignee: SUNTORY HOLDINGS LIMITED, Osaka (JP)

( * ) Notice: Subject to any disclaimer, the term of this patent is extended or adjusted under 35 U.S.C. 154(b) by 0 days.

(21) Appl. No.: 15/764,589

(22) PCT Filed: Sep. 21, 2016

(86) PCT No.: PCT/JP2016/077813
§ 371 (c)(1),
(2) Date: Mar. 29, 2018

(87) PCT Pub. No.: WO2017/057124
PCT Pub. Date: Apr. 6, 2017

(65) Prior Publication Data
US 2018/0280552 A1   Oct. 4, 2018

(30) Foreign Application Priority Data
Sep. 30, 2015  (JP) .................. 2015-193946

(51) Int. Cl.
*A61L 2/04* (2006.01)
*B67D 1/07* (2006.01)
(Continued)

(52) U.S. Cl.
CPC .................. *A61L 2/04* (2013.01); *A23L 2/46* (2013.01); *A23L 2/54* (2013.01); *B01F 1/00* (2013.01);
(Continued)

(58) Field of Classification Search
CPC ................ A61L 2/04; B01F 1/00; B67D 1/07
See application file for complete search history.

(56) References Cited

U.S. PATENT DOCUMENTS 5,064,097 A * 11/1991 Brog ..................... B01D 61/08
222/129
6,143,258 A    11/2000 Tamura et al.
(Continued)

FOREIGN PATENT DOCUMENTS

CN        1764594       4/2006
JP       11-104619      4/1999
(Continued)

OTHER PUBLICATIONS

International Search Report issued in PCT/JP2016/077813 and English translation thereof, dated Dec. 20, 2016.
(Continued)

*Primary Examiner* — Sean E Conley
(74) *Attorney, Agent, or Firm* — Greenblum & Bernstein, P.L.C.

(57) ABSTRACT

A beverage dispenser (1) includes a cold water tank (20) for storing cold water (50), a carbonation tank (30) disposed with at least a bottom portion thereof being submerged in the cold water (50) in the cold water thank (20), the carbonation tank being configured to generate carbonated water (60) by adding carbon dioxide gas to the cold water (50) supplied from the cold water tank (20), a carbonated water outlet passage (35) for taking out the carbonated water (60) from the carbonation tank (30) and a heater (41) for heating the cold water (50) in the cold water tank (20). In order to sterilize the above beverage dispenser (1), the heater (41) is caused to heat the cold water (50) in the cold water tank (20) to a temperature higher than a predetermined temperature, thereby to sterilize the cold water tank (20) and the carbonation tank (30). After the carbonated water (60) in the carbonation tank (30) is taken out via the carbonated water outlet passage (35), hot/warm water (70) in the cold water tank (20) is cooled.

5 Claims, 3 Drawing Sheets

(51) Int. Cl.
*B01F 1/00* (2006.01)
*A23L 2/46* (2006.01)
*A23L 2/54* (2006.01)
*B01F 3/04* (2006.01)

(52) U.S. Cl.
CPC ............ *B01F 3/04808* (2013.01); *B67D 1/07* (2013.01); *B01F 2003/049* (2013.01); *B01F 2215/0022* (2013.01)

(56) References Cited

U.S. PATENT DOCUMENTS

| | | |
|---|---|---|
| 2004/0238975 A1 | 12/2004 | Sakakibara et al. |
| 2006/0279007 A1 | 12/2006 | Sakakibara et al. |
| 2007/0222090 A1 | 9/2007 | Sakakibara et al. |
| 2007/0222091 A1 | 9/2007 | Sakakibara et al. |
| 2008/0226521 A1 | 9/2008 | Nakano et al. |
| 2008/0274248 A1 | 11/2008 | Sakakibara et al. |
| 2014/0239521 A1* | 8/2014 | Ergican ................ B67D 1/0058 261/115 |

FOREIGN PATENT DOCUMENTS

| | | |
|---|---|---|
| JP | 2005-238031 | 9/2005 |
| JP | 2011-258106 | 12/2011 |
| JP | 2015-40078 | 3/2015 |
| JP | 2015-193396 | 11/2015 |
| WO | 93/10035 | 5/1993 |

OTHER PUBLICATIONS

Extended European Search Report in Appl. No. 16851298.6, dated Mar. 15, 2019.

Office Action issued in China Counterpart Patent Appl. No. 201680057821.6, dated Mar. 20, 2019.

\* cited by examiner

METHOD OF STERILIZING BEVERAGE DISPENSER AND BEVERAGE DISPENSER

TECHNICAL FIELD

This disclosure relates to a method of sterilizing a beverage dispenser for dispensing at least carbonated water as drinking water and a beverage dispenser suitable for use with the sterilizing method.

RELATED ART

As a beverage dispenser capable of dispensing cold water and carbonated water as drinking water respectively, there is known a beverage dispenser having a cold water tank for storing cold water cooled by a cooler, and a carbonation tank for producing carbonated water by adding carbon dioxide gas to the cold water supplied from the cold water tank, so that the dispenser allows taking-out of the cold water from the cold water tank and taking-out of the carbonated water from the carbonation tank.

Conventionally, with such beverage dispenser, the cold water tank and the carbonation tank are provided separately from each other. However, Japanese patent application No. 2014-72120 proposes a beverage dispenser arranged such that a carbonation tank is disposed with at least a bottom portion of this carbonation tank being submerged in cold water in a cold water tank. This beverage dispenser provides an advantage of possibility to reduce its installing space.

SUMMARY

Problem to be Solved by Invention

Such beverage dispenser requires periodical sterilization thereof. In this regard, since the beverage dispenser proposed by Japanese patent application No. 2014-72120 has such non-conventional arrangement, no effective sterilizing method suited for this arrangement has not yet been conceived.

Thus, there remains a need for a method of sterilizing a beverage dispenser having such novel arrangement in an efficient manner as well as a beverage dispenser suitable for use with such sterilizing method.

Solution

A method of sterilizing a beverage dispenser relating to the present invention is a method of sterilizing a beverage dispenser for dispensing at least carbonated water, the beverage dispenser including:

a cold water tank having a cooler and configured to hold cold water cooled by the cooler;

a carbonation tank disposed with at least a bottom portion thereof being submerged in the cold water in the cold water thank, the carbonation tank being configured to generate carbonated water by adding carbon dioxide gas to the cold water supplied from the cold water tank;

a carbonated water outlet passage for taking out the generated carbonated water from the carbonation tank; and a heater for heating the cold water in the cold water tank; the method comprising the steps of:

causing the heater to heat the cold water in the cold water tank to a temperature higher than a predetermined temperature, thereby to sterilize the cold water tank and the carbonation tank; and taking out the carbonated water in the carbonation tank via the carbonated water outlet passage and then causing the cooler to cool hot/warm water in the cold water tank.

With the above-described arrangement, the cold water tank is thermally sterilized by causing the heater to heat the cold water in the cold water tank. In this, since the carbonation tank is disposed with at least a bottom portion thereof being submerged in the cold water in the cold water tank, the carbonated water held in the carbonation tank can be heated simultaneously. With this, the carbonation tank can be sterilized simultaneously. Therefore, the sterilization can be carried out in an efficient manner with the single heater, without need to provide such heaters in the cold water tank and the carbonation tank respectively. Further, after the sterilization, the hot/warm water in the cold tank is to be cooled again. In this, since carbonic acid has been lost from the carbonated water due to the heating, this water even cooled again will be of poor quality, thus being useless. Also, for cooling the hot/warm water in the cold water tank, the heated carbonated water in the carbonation tank will be cooled also. But, cooling of such carbonated water which is to become useless after cooling will be wasteful. Then, according to the above-described inventive arrangement, the hot/warm water in the cold water tank is cooled after the carbonated water in the carbonation tank has been taken out. So, energy required for cooling carbonated water in the carbonation tank can be saved. In this way, with the inventive arrangement above, efficient sterilization process is made possible.

According to one embodiment, in the beverage dispenser, a portion of the carbonated water outlet passage is connected at least to the cold water tank, so that the carbonated water taken out of the carbonation tank is supplied to the cold water tank.

With the above-described arrangement, the carbonated water which has become useless as carbonated water is not disposed of, but supplied to the cold water tank for reuse instead. Thus, waste can be avoided as a whole.

According to one preferred embodiment, the carbonated water outlet passage is provided for dispensing the carbonated water as drinking water;

the beverage dispenser further includes a cold water outlet passage for taking out the cold water from the cold water tank as drinking water and a bypass passage connected to the carbonated water outlet passage and the cold water outlet passage; and the carbonated water is supplied from the carbonation tank to the cold water tank via the carbonated water outlet passage and the cold water outlet passage.

With the above-described arrangement, with the beverage dispenser capable of dispensing cold water and carbonated water as drinking water respectively via the carbonated water outlet passage and the cold water outlet passage, by providing this dispenser with a bypass passage connected to the carbonated water outlet passage and the cold water outlet passage, carbonated water can be supplied from the carbonation tank to the cold water tank, with utilization of the carbonated water outlet passage and the cold water outlet passage. In this way, there is no need to provide an additional passage for supplying carbonated water from the carbonation tank to the cold water tank, so the sterilization process can be effected without any superfluity in the device arrangement.

A beverage dispenser according to the present invention is a beverage dispenser for dispensing drinking water, the dispenser comprising:

a cold water tank having a cooler and configured to hold cold water cooled by the cooler;

a carbonation tank disposed with at least a bottom portion thereof being submerged in the cold water in the cold water thank, the carbonation tank being configured to generate carbonated water by adding carbon dioxide gas to the cold water supplied from the cold water tank;

a carbonated water outlet passage for taking out the generated carbonated water from the carbonation tank as the drinking water;

a heater for heating the cold water in the cold water tank; and a pipe passage capable of feeding the carbonated water in the carbonation tank to the cold water tank.

According to one embodiment, the beverage dispenser further comprises a bypass passage connected to the carbonated water outlet passage and the cold water outlet passage;

wherein the pipe passage consists of the carbonated water outlet passage, the cold water outlet passage and the bypass passage; and wherein the carbonated water in the carbonation tank can be supplied to the cold water tank via the carbonated water outlet passage, the cold water outlet passage and the bypass passage.

With the beverage dispenser described above, the above-described sterilization method can be embodied in a suitable manner.

EMBODIMENT

A method of sterilizing a beverage dispenser and the beverage dispenser therefor will be explained next with reference to the accompanying drawings. A method of sterilizing a beverage dispenser 1 relating to the present invention is a method of sterilizing such beverage dispenser 1 for dispensing at least carbonated water 60 as drinking water. The beverage dispenser 1 includes a cold water tank 20, a carbonation tank 30, a carbonated water outlet passage 35 and a heater 41. The cold water tank 20 has a cooler 21 and is configured to hold cold water 50 cooled by the cooler 21. The carbonation tank 30 is disposed with at least its bottom portion being submerged in the cold water 50 held in the cold water tank 20 and is configured to generate carbonated water 60 by adding carbon dioxide gas to the cold water 50 supplied from the cold water tank 20. The carbonated water outlet passage 35 is provided for taking out the generated carbonated water 60 from the carbonation tank 30. The heater 41 is provided for heating the cold water 50 in the cold water tank 20. Then, according to an inventive method of sterilizing the beverage dispenser 1 above, the heater 41 is caused to heat the cold water 50 in the cold water tank 20 to a temperature higher than a predetermined temperature, thereby to sterilize the cold water tank 20 and the carbonation tank 30. Then, after taking out the carbonated water 60 in the carbonation tank 30 via the carbonated water outlet passage 35, the cooler 21 is operated to cool hot/warm water 70 in the cold water tank 20. This achieves efficient sterilization of the unconventional beverage dispenser 1. Next, the method of sterilizing the beverage dispenser and such beverage dispenser for use with such method will be explained in greater details.

Figure 1:
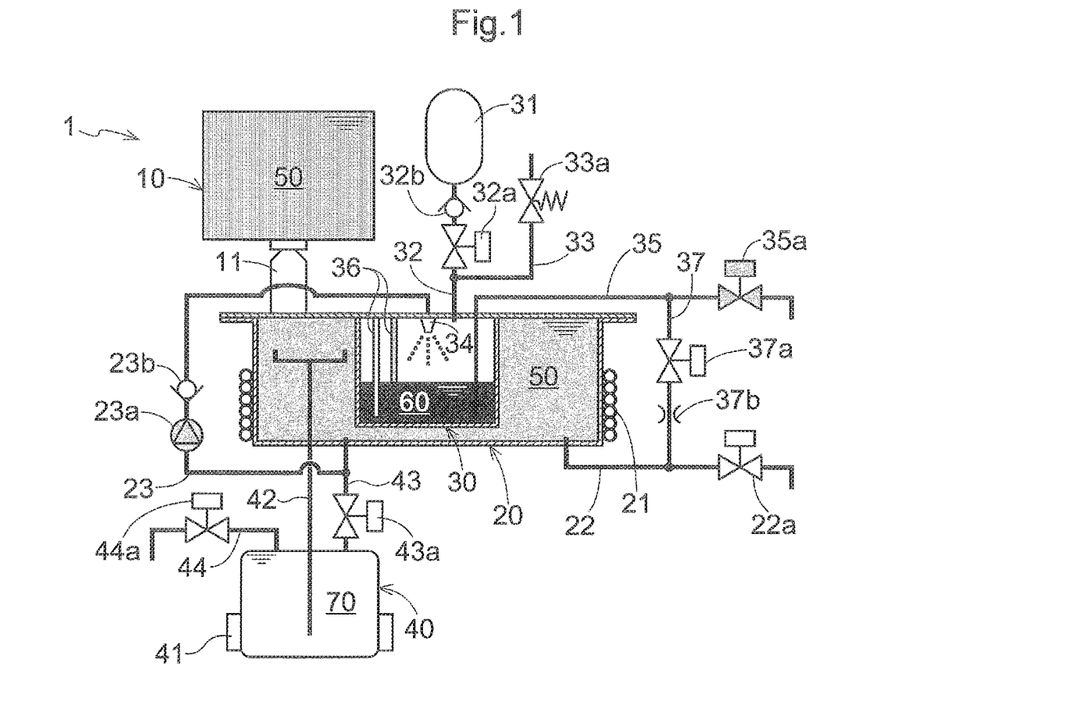
FIG. 1 is a schematic configuration diagram of a beverage dispenser.

As shown in FIG. 1, the beverage dispenser 1 relating to the instant embodiment includes, mainly, a purified water tank 10, the cold water tank 20 for cooling and storing purified water 50 supplied from the purified water tank 10, the carbonation tank 30 configured to generate carbonated water by adding carbon dioxide gas to the cold water 50 supplied from the cold water tank 20, and a hot/warm water tank 40 configured to takeout a portion of the cold water 50 held in the cold water tank 20 and then heating and storing this water.

The purified water tank 10 stores therein an amount of purified water 50 such as mineral water. This purified water tank 10 is disposed upwardly of the cold water tank 20. A purified water supply passage 11 provided at the bottom portion of the purified water tank 10 is connected to the cold water tank 20, so that the purified water 50 is supplied from the purified water tank 10 to the cold water tank 20 via this purified water supply passage 11.

The cold water tank 20 includes, as a "cooler" thereof, a cooling coil 21 which is disposed in a spiral manner in its outer lateral face and allowing circulation of coolant inside it. By this cooling coil 21, the purified water 50 supplied from the purified water tank 10 is cooled and this cooled purified water 50 ("cold water") is stored in the cold water tank 20. Further, the cold water tank 20 includes an unillustrated temperature sensor for detecting a temperature of the purified water 50 (cold water). The cold water tank 20 further includes a first cold water outlet passage (corresponding to a "cold water outlet passage") 22 for taking out the cold water 50 from the cold water tank 20 as "drinking water". In response to an opening/closing operation of an electromagnetic valve 22a incorporated in the first cold water outlet passage 22, the cold water 50 is dispensed from the cold water tank 20 via the first cold water outlet passage 22. The cold water tank 20 still further includes a second cold water outlet passage 23 for supplying the cold water 50 to the carbonation tank 30. In response to an operation of a high-pressure pump 23a provided in the second cold water outlet passage 23, the cold water 50 is supplied from the cold water tank 20 to the carbonation tank 30. Incidentally, within the second cold water outlet passage 23 on the side closer to the carbonation tank than the high-pressure pump 23a, there is incorporated a check valve 23b for checking reverse flow of the cold water 50 and the carbon dioxide gas toward the cold water tank 20.

The carbonation tank 30 is disposed with at least a bottom portion thereof being submerged in the cold water 50 held in the cold water tank 20. In the instant embodiment, a top face of the carbonation tank 30 and a top face of the cold water tank 20 are disposed flush with each other and the carbonation tank 30 is accommodated within the cold water tank 20.

The carbonation tank 30 is connected to a carbon dioxide gas cylinder 31 via a carbon dioxide gas supply passage 32. In response to an operation of an electromagnetic valve 32a incorporated in the carbon dioxide gas supply passage 32, carbon dioxide gas is supplied from the carbon dioxide gas cylinder 31 to the carbonation tank 30; and with pressure regulation by an unillustrated pressure regulator, the inside of the carbonation tank 30 is filled with the carbon dioxide gas at a predetermined pressure. Further, within the carbon dioxide gas supply passage 32 on the side closer to the carbon dioxide gas cylinder 31 than the electromagnetic valve 32a, there is incorporated a check valve 32b for checking reverse flow of the carbon dioxide gas toward the carbon dioxide gas cylinder 31. Still further, within the carbon dioxide gas supply passage 32 on the side closer to the carbonation tank 30 than the opening/closing (electromagnetic) valve 32a, there is connected a bypass passage 33 incorporating a safety valve 33a. In operation, when the inside pressure of the carbonation tank 30 rises above a predetermined limit, the carbon dioxide gas is allowed to escape from the carbonation tank 30 via this bypass passage 33, thus reducing the inside pressure for securing safety.

The carbonation tank 30 is connected to the second cold water outlet passage 23 extending from the cold water tank 20 and the cold water 50 supplied from the second cold water outlet passage 23 is sprayed into the carbonation tank 30 in the form of mist via a spray nozzle 34. As this cold water 50 sprayed from the spray nozzle 34 absorbs the carbon dioxide gas inside the carbonation tank 30, the carbonated water 60 is generated. And, the carbonation tank 30 includes a carbonated water outlet passage 35 for taking out the carbonated water 60 from the carbonation tank 30 as "drinking water". A terminal end of the carbonated water outlet passage 35 on the side of the carbonation tank 30 is extended to vicinity of the bottom portion of the carbonation tank 30. Since the inside pressure of the carbonation tank 30 has been raised, when the electromagnetic valve 35a provided in the carbonated water outlet passage 35 is opened, due to a resultant pressure difference, the carbonated water 60 will be supplied from inside the carbonation tank 30 via the carbonated water outlet passage 35. Still further, the carbonation tank 30 includes a water level sensor 36 for determining a water level of the carbonated water 60. When the water level sensor 36 detects drop of water level, the high-pressure pump 23a is activated, so that the cold water 50 will be sprayed into the carbonation tank 30, thus generating new additional carbonated water 60 (in FIG. 1, there is shown a state in which in association with takeout of an amount of carbonated water 60 in response to opening of the electromagnetic valve 35a, the water level sensor 36 detects resultant drop in the water level, thus, the high-pressure pump 23a is operated to generate new carbonated water 60).

Moreover, a bypass passage 37 is connected to the carbonated water outlet passage 35 and the first cold water outlet passage 22, so that an amount of the carbonated water 60 held in the carbonation tank 30 can be supplied to the cold water tank 20. More particularly, the bypass passage 37 is connected to a portion of the carbonated water outlet passage 35 downstream the electromagnetic valve 35a thereof and to a portion of the first cold water outlet passage 22 downstream the electromagnetic valve 22a thereof, respectively. As described above, since the inside pressure of the carbonation tank 30 has been raised, by opening the electromagnetic valve 37a incorporated in the bypass passage 37, due to a resultant pressure difference, the carbonated water 60 can be supplied from the carbonation tank 30 to the cold water tank 20. Further, the bypass passage 37 further incorporates a throttle valve 37b, so that by operating this throttle valve 37b, it is possible to adjust the amount of the carbonated water 60 to be supplied to the cold water tank 20.

The hot/warm water tank 40 is provided for storing an amount of hot/warm water 70 for hot-water sterilization of the cold water tank 20 and the carbonation tank 30. In operation, by opening an electromagnetic valve 44a incorporated in a hot/warm water outlet passage 44, the hot/warm water 70 is supplied from inside the hot/warm water tank 40. The hot/warm water tank 40 includes a heater 41 for heating water inside the hot/warm water tank 40, so that the cold water 50 received from the cold water tank 20 via a cold water inlet passage 42 can be heated. Further, the hot/warm water tank 40 includes a hot/warm water inlet passage 43 for feeding the hot/warm water 70 (including the cold water 50 heated by the heater 41) into the cold water tank 20. Incidentally, the hot/warm water inlet passage 43 incorporates an electromagnetic valve 43a. With the hot/warm water tank 40 for its hot-water sterilization treatment of the cold water tank 20 and the carbonation tank 30, the cold water 50 inside the cold water tank 20 is sent to the hot/warm water tank 40 via the cold water inlet passage 42 and by an amount of the received cold water 50, the cold water 50 inside the hot/warm water tank 40 is sent to the cold water tank 20 via the hot/warm water inlet passage 43. And, in parallel with the above, the heater 41 heats the water inside the hot/warm water tank 40 including the cold water 50 received from the cold water tank 20. Namely, between the cold water tank 20 and the hot/warm water tank 40, water (cold water 50 and hot/warm water 70) is circulated while being heated by the heater 41. With continuation of this process, the cold water 50 in the cold water tank 20 is substantially heated by the heater 41, so that the cold water tank 20 may be filled with the hot/warm water 70.

Incidentally, the beverage dispenser includes an unillustrated controller and switches for various operations which will be described later, so that by the controller, operations to be described later may be effected according to operations of the various switches of various parts of the beverage dispenser. Further, detection signals of the temperature sensor, the pressure sensor and the water-level sensor described above are sent to the controller, so that operations of the respective parts corresponding to such detection results will be effected by the controller.

Next, operations of this beverage dispenser will be described with reference to the accompanying drawings. Incidentally, the instruments (electromagnetic valves, etc.) operated in the operations of the respective drawings are colored. Firstly, a preparation operation prior to use will be explained.

[Preparation Operation]

By depressing an unillustrated main switch of the beverage dispenser 1, a preparation operation is initiated. First, in this preparation operation, the purified water 50 is supplied from the purified water tank 10 to the cold water tank 20. When the cold water tank 20 is filled with the purified water 50, a cooling operation by the cooling coil 21 is started, so that the purified water 50 in the cold water tank 20 is cooled until it reaches a set temperature (e.g. 5-10° C.). Further, in parallel with the supplying and cooling of the purified water 50, the electromagnetic valve 32a of the carbon dioxide gas supply passage 32 is opened to start supplying of carbon dioxide gas to the carbonation tank 30. And, this supplying of carbon dioxide gas to the carbonation tank 30 is continued until the inside pressure of the carbonation tank 30 becomes a pressure higher than a predetermined value. Further, the lower the water temperature and the higher the pressure of the carbon dioxide gas, the higher the absorption ratio of the carbon dioxide gas to the water. Thus, when the purified water 50 has been cooled to the set temperature and the inside pressure of the carbonation tank 30 has risen to reach the predetermined value, the high-pressure pump 23a is activated to spray the cooled purified water 50 (cold water) into the carbonation tank 30. With the above arrangement of supplying the cold water 50 to the carbonation tank 30 filled with carbon dioxide gas under a high pressure together with the further arrangement of effecting this supplying it in the form of mist, the contact area between the cold water 50 and the carbon dioxide gas is increased, whereby the carbonated water 60 is generated in an efficient manner. And, when the carbonated water 60 has been generated to reach a predetermined water level, the preparation operation is completed.

[Normal Operation]

After completion of the preparation operation, the process enters a normal operation state. In this, in response to depression of a cold water dispensing switch for instance, the cold water 50 will be dispensed via the first cold water outlet passage 22. In response to depression of a carbonated water dispensing switch for instance, the carbonated water 60 will be dispensed via the carbonated water outlet passage 35. Further, in this normal operation state, a cooling operation by the cooling coil 21 is effected when needed in accordance with a temperature detected by the unillustrated temperature sensor in order to maintain the cold water 50 inside the cold water tank 20 within a predetermined temperature range. In the beverage dispenser according to the instant embodiment, the carbonation tank 30 is submerged in the cold water 50 inside the cold water tank 20. So, as the temperature of the cold water 50 inside the cold water tank 20 is maintained within the predetermined temperature range, the carbonated water 60 inside the carbonation tank 30 is maintained also within the predetermined temperature range. Further, in order to prevent loss of carbon dioxide in the carbonated water 60, supplying of carbon dioxide gas into the carbonation tank 30 is effected by the unillustrated pressure regulator so as to maintain the inside pressure of the carbonation tank 30 within a predetermined pressure range. Moreover, in preparation for a subsequent sterilization operation to be described later, when the hot/warm water tank 40 has been filled with cold water 50 held in the cold water tank 20 via the cold water inlet passage 42, thus filling the hot/warm water tank 40 with the cold water 50, a heating operation by the heater 41 will be effected thereafter (or the hot/warm water 70 will be supplied to the hot/warm water tank 40 via the hot/warm water outlet passage 44). When the temperature is detected by the unillustrated temperature sensor and this temperature rises beyond a predetermined temperature (e.g. 80° C.), the heating operation by the heater will be stopped. Thereafter, a heating operation by the heater will be effected occasionally when needed so as to maintain the temperature within the predetermined temperature range.

[Sterilization Operation]

Figure 2:
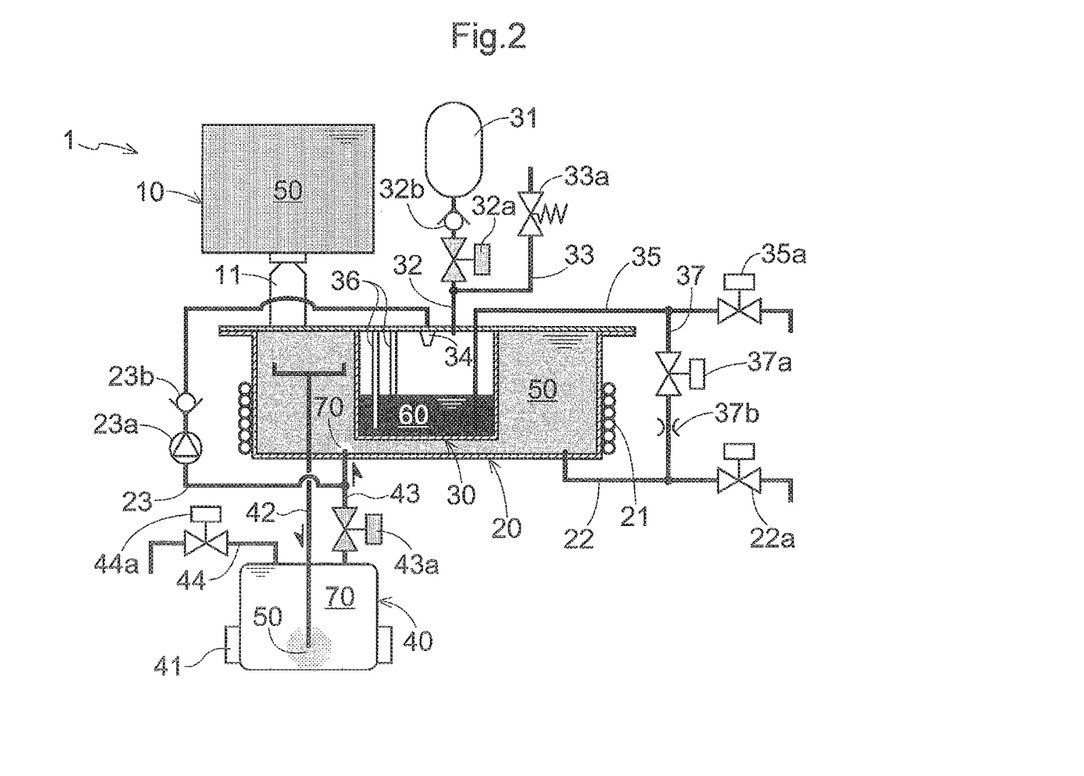
FIG. 2 is an explanatory view of the beverage dispenser during its sterilizing operation.
Figure 3:
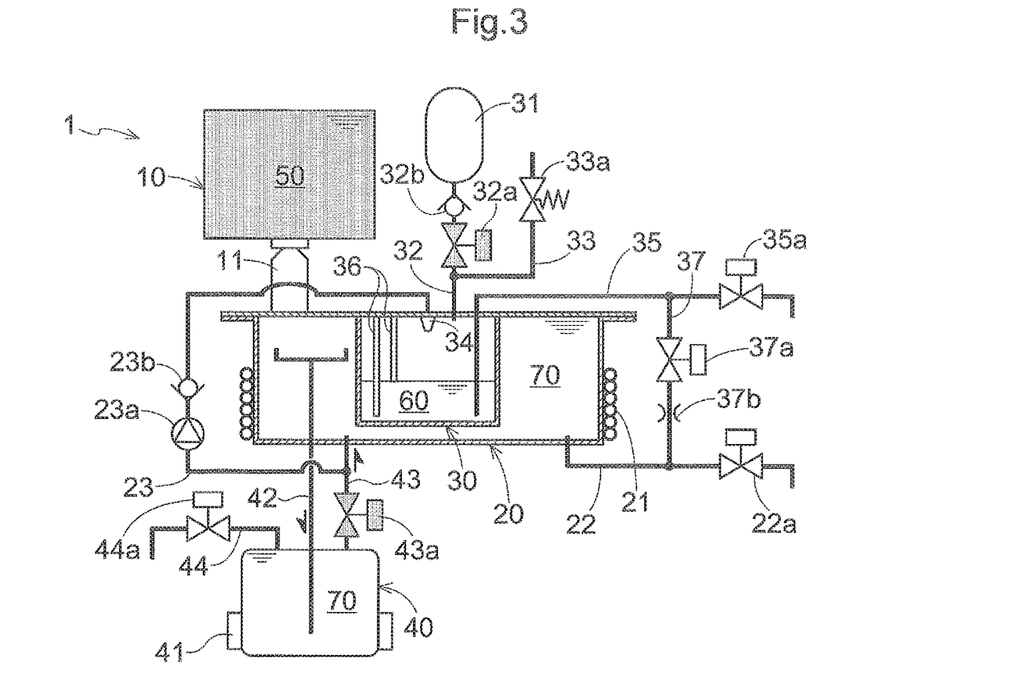
FIG. 3 is an explanatory view of the beverage dispenser during its sterilizing operation.

For instance, in response to depression of a sterilization operation switch, in the beverage dispenser 1, a sterilization process of the cold water tank 20 and the carbonation tank 30 is initiated. First, as shown in FIG. 2, the electromagnetic valve 32a in the carbon dioxide gas supply passage 32 is closed to shut off supply of carbon dioxide gas. And, the electromagnetic valve 43a in the hot/warm water inlet passage 43 is opened to feed the hot/warm water 70 from the hot/warm water tank 40 to the cold water tank 20 and to feed the cold water 50 from the cold water tank 20 to the hot/warm water tank 40. Simultaneously, the heater 41 too is operated, so that by this heater 41, the water present inside the hot/warm water tank 40 including the cold water 50 received from the cold water tank 20 is heated. In this way, between the cold water tank 20 and the hot/warm water tank 40, water (cold water 50 and hot/warm water 70) is circulated while being heated by the heater 41 and the cold water 50 in the cold water tank 20 is substantially heated by the heater 41, so that the temperature of the water inside the cold water tank 20 rises progressively. With continuation of this process for an extended period, as shown in FIG. 3, the water temperature inside the cold water tank 20 will rise sufficiently and the cold water tank 20 will be filled with the hot/warm water 70 (e.g. 80° C.), whereby hot-water sterilization of the cold water tank 20 is effected. Further, with the beverage dispenser 1 according to the instant embodiment, since the carbonation tank 30 is submerged in the water inside the cold water tank 20, in association with the rise of the water temperature inside the cold water tank 20, the water temperature of the carbonated water 60 inside the carbonation tank 30 will rise also. As a result, the water temperature of the carbonated water 60 inside the carbonation tank 30 too will rise sufficiently, so that sterilization of this carbonation tank 30 will be effected also. In this way, with the beverage dispenser 1 of this embodiment, by elevating the temperature of the cold water 50 in the cold water tank 20 by the heater 41 to a temperature higher than a predetermined temperature, both the cold water tank 20 and the carbonation tank 30 are sterilized.

After completion of the hot-water sterilization of the cold water tank 20 and the carbonation tank 30, the hot/warm water 70 in the cold water tank 20 is cooled to return the process to the normal operation state. In this, carbon dioxide gas has already been lost from the carbonated water 60 due to the heating, so this water, even if cooled, will be of poor quality, thus being useless. Further, in order to cool the hot/warm water 70 in the cold water tank 20, the heated carbonated water 60 in the carbonation tank 30 is to be cooled also. However, cooling of the carbonated water 60 which will become useless after cooling will be wasteful. Then, with the beverage dispenser 1 according to the instant embodiment, after the carbonated water 60 inside the carbonation tank 30 is taken out via the carbonated water outlet passage 35, the hot/warm water 70 inside the cold water tank 20 is cooled by the cooler 21. Further, in the instant embodiment, the carbonated water 60 taken out of the carbonation tank 30 is returned to the cold water tank 20 for reuse. With this arrangement, energy required for cooling the carbonated water 60 in the carbonation tank 30 can be saved and there occurs no waste since there is no disposal of heated carbonated water 60.

Figure 4:
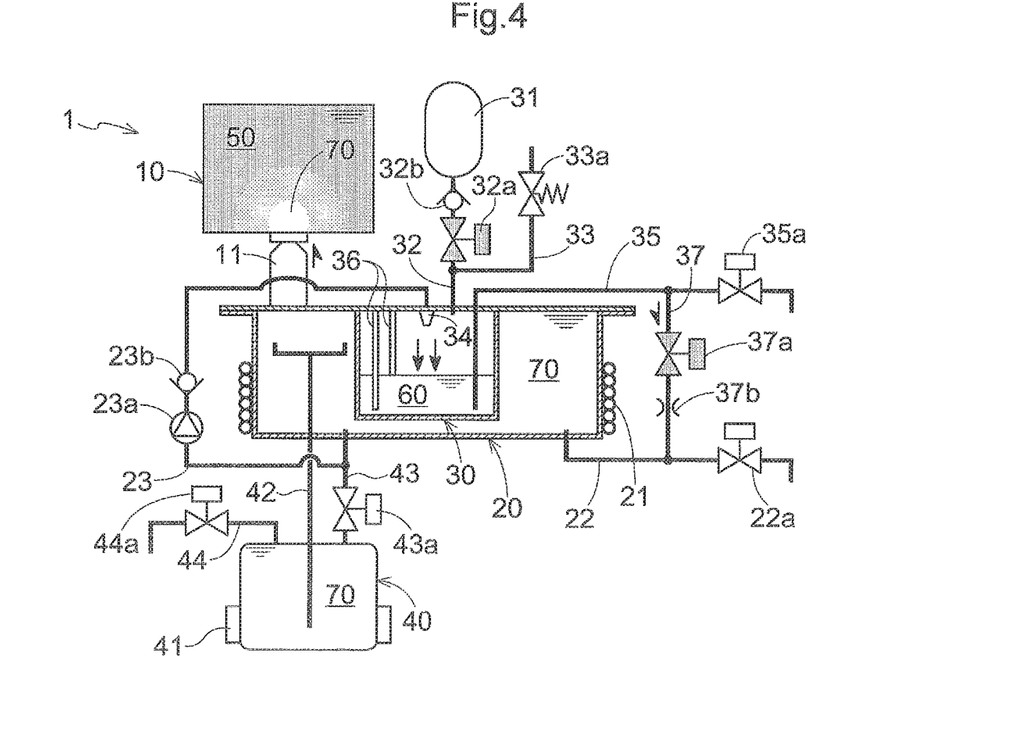
FIG. 4 is an explanatory view of the beverage dispenser during its sterilizing operation.
Figure 5:
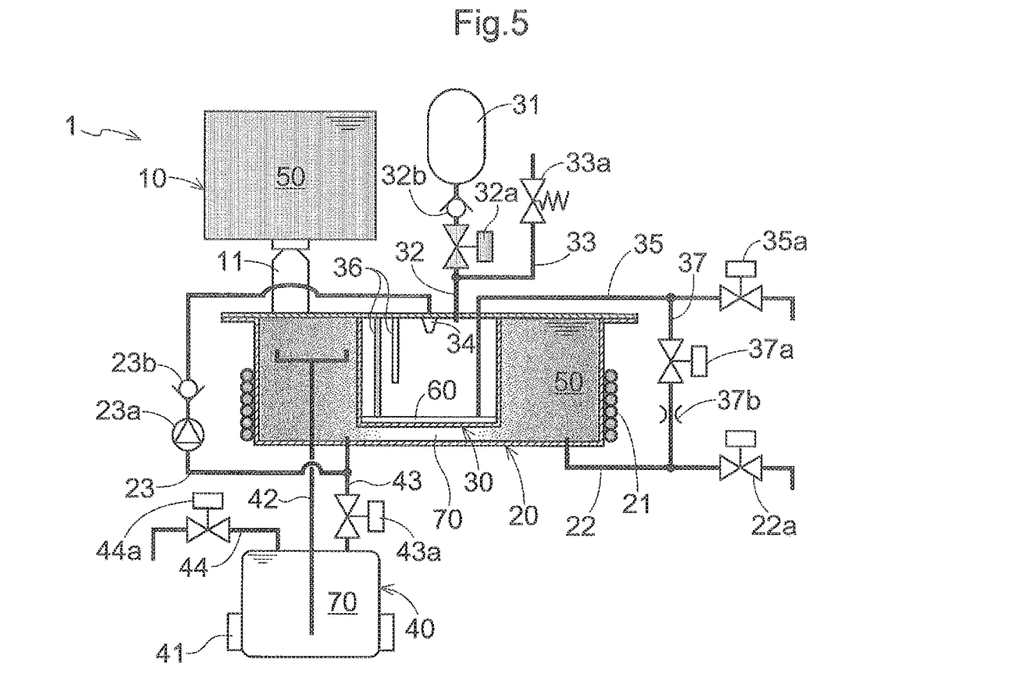
FIG. 5 is an explanatory view of the beverage dispenser during its sterilizing operation.
Figure 6:
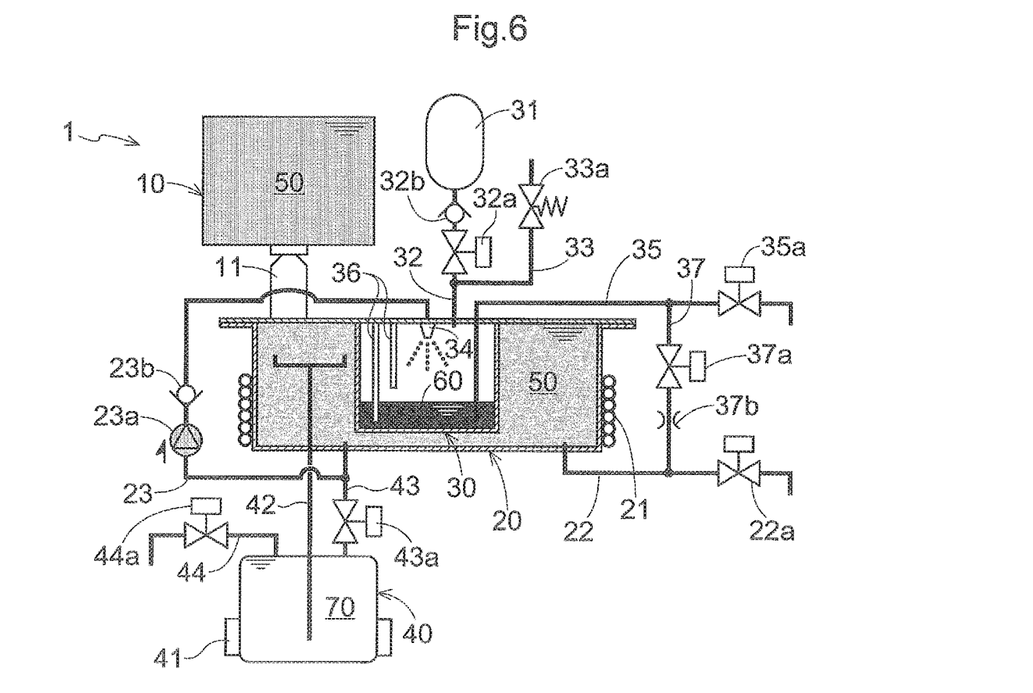
FIG. 6 is an explanatory view of the beverage dispenser during its sterilizing operation.

More particularly, first, as shown in FIG. 4, the electromagnetic valve 43a of the hot/warm water inlet passage 43 is closed and the electromagnetic valve 37a of the bypass passage 37 is opened. Inside the carbonation tank 30, the pressure has been dropped relative to the pressure at the time of the normal operation state due to the blocking of carbon dioxide gas supply during the above-described sterilization operation. Notwithstanding, there still remains a sufficiently high pressure. So, under this remaining pressure, the carbonated water 60 is supplied from the carbonation tank 30 to the cold water tank 20 via the carbonated water outlet passage 35, the bypass passage 37 and the first cold water outlet passage 22. In this, by the amount of supplied carbonated water 60, there occurs reverse flow of the hot/warm water 70 inside the cold water tank 20 to the purified water tank 10. And, when the water level sensor 36 detects taking-out of a sufficient amount of the carbonated water 60, the electromagnetic valve 37a of the bypass passage 37 is closed. Thereafter, a cooling operation by the cooling coil 21 for cooling the hot/warm water 70 inside the cold water tank 20 is effected (see FIG. 5). When the water temperature inside the cold water tank 20 drops to a temperature lower than the predetermined temperature (5-10° C., etc.), supplying of carbon dioxide gas to the carbonation tank 30 is effected. When the inside pressure of the carbonation tank 30 rises beyond the predetermined pressure, the high-pressure pump 23a is operated, whereby the cold water 50 is sprayed into the carbonation tank 30 to generate carbonated water 60 (see FIG. 6). And, when the water level sensor 37 detects generation of carbonated water 60 by an amount greater than the predetermined amount, the high-pressure pump 23a is stopped. Thereafter, the beverage dispenser 1 returns to the normal operation state.

The beverage dispenser 1 relating to the instant embodiment operates as described above. In particular, with the beverage dispenser 1 relating to the instant embodiment, in its sterilization operation, subsequently to completion of hot-water sterilization of the cold water tank 20 and the carbonation tank 30, after the carbonated water 60 present in the carbonation tank 30 is taken out via the carbonated water outlet passage 35, the hot/warm water 70 inside the cold water tank 20 is cooled by the cooler 21. Thus, the dispenser achieves the further advantage of allowing efficient sterilization process.

[Other Embodiments]

In the foregoing embodiment, there was explained the arrangement wherein after completion of the hot-water sterilization of the cold water tank 20 and the carbonation tank 30, the carbonated water 60 in the carbonation tank 30 is supplied from this carbonation tank 30 to the cold water tank 20 via the carbonated water outlet passage 35, the bypass passage 37 and the first cold water outlet passage 22. However, the present invention is not limited thereto. The carbonated water 60 inside the carbonation tank 30 may be taken out of the dispenser via the carbonated water outlet passage 35 without being supplied to the cold water tank 20. Further, rather than supplying to the cold water tank 20 via the carbonated water outlet passage 35, the bypass passage 37 and the first cold water outlet passage 22 or using the bypass passage 37, there may be additionally provided a pipe passage that directly connects the carbonation tank 30 to the cold water tank 20 or a pipe passage that directly connects the carbonated water outlet passage 35 to the cold water tank 20, so that after completion of hot-water sterilization of the cold water tank 20 and the carbonation tank 30 with using such additional passage, the carbonated water 60 in the carbonation tank 30 may be supplied to the cold water tank 20.

Aside from the above, it should be understood that the embodiments disclosed in the above description are only illustrative in all respects thereof and the scope of the present is not limited thereto. Those skilled in the art will readily understand that various modifications are possible as needed without departing from the essence of the present invention. Therefore, all other embodiments modified within a range not departing from the essence of the present invention are contained also within the scope of the present invention, as a matter of course.

INDUSTRIAL APPLICABILITY

The present invention is applicable for sterilization of a beverage dispenser for example.

DESCRIPTION OF REFERENCE MARKS/NUMERALS

1: beverage dispenser
20: cold water tank
21: cooler
22: cold water outlet passage
30: carbonation tank
35: carbonated water outlet passage
37: bypass passage
41: heater
50: cold water
60: carbonated water

The invention claimed is:

1. A method of sterilizing a beverage dispenser for dispensing at least carbonated water, the beverage dispenser including:
a cold water tank having a cooler and configured to hold cold water cooled by the cooler;
a carbonation tank disposed with at least a bottom portion thereof being submerged in the cold water in the cold water thank, the carbonation tank being configured to generate carbonated water by adding carbon dioxide gas to the cold water supplied from the cold water tank;
a carbonated water outlet passage for taking out the generated carbonated water from the carbonation tank; and
a heater for heating the cold water in the cold water tank;
the method comprising the steps of:
causing the heater to heat the cold water in the cold water tank to a temperature higher than a predetermined temperature, thereby to sterilize the cold water tank and the carbonation tank; and
taking out the carbonated water in the carbonation tank via the carbonated water outlet passage and then causing the cooler to cool hot/warm water in the cold water tank.

2. The sterilizing method of claim 1, wherein a portion of the carbonated water outlet passage is connected at least to the cold water tank, so that the carbonated water taken out of the carbonation tank is supplied to the cold water tank.

3. The sterilizing method of claim 2, wherein:
the carbonated water outlet passage is provided for dispensing the carbonated water as drinking water;
the beverage dispenser further includes a cold water outlet passage for taking out the cold water from the cold water tank as drinking water and a bypass passage connected to the carbonated water outlet passage and the cold water outlet passage; and
the carbonated water is supplied from the carbonation tank to the cold water tank via the carbonated water outlet passage and the cold water outlet passage.

4. A beverage dispenser for dispensing drinking water, the dispenser comprising:
a cold water tank having a cooler and configured to hold cold water cooled by the cooler;
a carbonation tank disposed with at least a bottom portion thereof being submerged in the cold water in the cold water thank, the carbonation tank being configured to generate carbonated water by adding carbon dioxide gas to the cold water supplied from the cold water tank;
a cold water outlet passage for taking out the cold water from the cold water tank as drinking water, and a first valve of the cold water outlet passage being configured to open and close to selectively dispense cold water from the cold water outlet passage;
a carbonated water outlet passage for taking out the generated carbonated water from the carbonation tank as drinking water, and a second valve of the carbonated water outlet passage being configured to open and close to selectively dispense the carbonated water from the carbonated water outlet passage;

wherein the first valve and the second valve are provided separately from each other;

a heater for heating the cold water in the cold water tank; and a pipe passage that includes the cold water outlet passage and the carbonated water outlet passage, wherein the pipe passage is capable of feeding the carbonated water in the carbonation tank to the cold water tank, wherein the pipe passage is configured to selectively communicate an interior of the carbonation tank with an interior of the cold water tank, the pipe passage having a first end positioned proximate a bottom of the carbonation tank and a second end positioned proximate a bottom of the cold water tank.

5. The beverage dispenser of claim 4, wherein:

the beverage dispenser further comprises a bypass passage connected to the carbonated water outlet passage and the cold water outlet passage;

wherein the pipe passage consists of the carbonated water outlet passage, the cold water outlet passage and the bypass passage; and wherein the carbonated water in the carbonation tank can be supplied to the cold water tank via the carbonated water outlet passage, the cold water outlet passage and the bypass passage.

\* \* \* \* \*

UNITED STATES PATENT AND TRADEMARK OFFICE
CERTIFICATE OF CORRECTION

PATENT NO. : 10,857,248 B2  
APPLICATION NO. : 15/764589  
DATED : December 8, 2020  
INVENTOR(S) : H. Hanano Page 1 of 1

It is certified that error appears in the above-identified patent and that said Letters Patent is hereby corrected as shown below:

On the Title Page

Item (57) Abstract, Line 4, please change "thank" to --tank--.

In the Claims

Column 10, Line 17, Claim 1, Line 8, please change "thank" to --tank--.
Column 10, Line 54, Claim 4, Line 7, please change "thank" to --tank--.

Signed and Sealed this  
Thirteenth Day of July, 2021

Drew Hirshfeld  
*Performing the Functions and Duties of the*  
*Under Secretary of Commerce for Intellectual Property and*  
*Director of the United States Patent and Trademark Office*